(12) United States Patent
LoGuercio (10) Patent No.: US 12,220,338 B2
(45) Date of Patent: Feb. 11, 2025

(54) MODIFIABLE HOT/COLD THERAPY KNEE BRACE KIT

(71) Applicant: DJO, LLC, Carlsbad, CA (US)

(72) Inventor: Donald P. LoGuercio, Scottsdale, AZ (US)

(73) Assignee: DJO, LLC, Carlsbad, CA (US)

( * ) Notice: Subject to any disclaimer, the term of this patent is extended or adjusted under 35 U.S.C. 154(b) by 742 days.

(21) Appl. No.: 17/467,862

(22) Filed: Sep. 7, 2021

(65) Prior Publication Data

US 2022/0071790 A1 Mar. 10, 2022

Related U.S. Application Data

(60) Provisional application No. 63/074,529, filed on Sep. 4, 2020.

(51) Int. Cl.
*A61F 5/00* (2006.01)
*A61F 5/01* (2006.01)
*A61F 7/02* (2006.01)
*A61F 7/00* (2006.01)

(52) U.S. Cl.
CPC ............. *A61F 5/0106* (2013.01); *A61F 7/02* (2013.01); *A61F 2007/0042* (2013.01); *A61F 2007/023* (2013.01)

(58) Field of Classification Search
USPC ................................ 602/26, 2; 607/96–114
See application file for complete search history.

(56) References Cited

U.S. PATENT DOCUMENTS

| 5,148,804 | A | * | 9/1992 | Hill | ............................ A61F 7/10 607/108 |
|---|---|---|---|---|---|
| 5,514,155 | A | | 5/1996 | Daneshvar | |
| 8,282,587 | B2 | * | 10/2012 | McSpadden | ........... A61F 5/0123 602/2 |
| 8,314,283 | B2 | * | 11/2012 | Kingsford | ........... A61B 5/02233 602/41 |
| 10,363,159 | B1 | | 7/2019 | LoGuercio | |
| 11,559,427 | B2 | * | 1/2023 | Kilbey | ...................... A61F 7/02 |

(Continued)

FOREIGN PATENT DOCUMENTS

KR 20150128519 A * 11/2015

OTHER PUBLICATIONS

KR 20150128519 A Translation (Year: 2015).*

*Primary Examiner* — Kim M Lewis
(74) *Attorney, Agent, or Firm* — Veros Legal Solutions, LLP (57) ABSTRACT

A knee brace kit includes a wrap having opposed inner and outer surfaces, and a body and straps extending from the body. The outer surface carries a first engagement element of a hook-and-loop engagement, the straps terminate at tips, and the inner surface at the tips carries a second engagement element of the hook-and-loop engagement complemental to the first engagement element. A hole in the wrap is located such that, when the wrap is worn by a person, the hole is disposed over a knee of the person and the straps are wrapped above and below the hole, defining an applied arrangement of the wrap. There are a plurality of trim lines indicated on the body, which, when the wrap is trimmed along the trim lines, maintain the applied arrangement of the straps with respect to the hole.

12 Claims, 8 Drawing Sheets

(56) References Cited

U.S. PATENT DOCUMENTS

| | | |
|---|---|---|
| 11,648,143 B2* | 5/2023 | Tessier .................. A61F 5/0123 |
| | | 602/26 |
| 2010/0152823 A1 | 6/2010 | Muchowicz |
| 2014/0330187 A1* | 11/2014 | Perez ...................... A61F 5/028 |
| | | 602/19 |
| 2017/0055687 A1 | 3/2017 | Diaz |
| 2020/0060859 A1 | 2/2020 | LoGuercio |

* cited by examiner

MODIFIABLE HOT/COLD THERAPY KNEE BRACE KIT

CROSS-REFERENCE TO RELATED APPLICATIONS

This application claims the benefit of U.S. Provisional Application No. 63/074,529, filed Sep. 4, 2020, which is hereby incorporated by reference.

FIELD

The present invention relates generally to medical devices, and more particularly to devices for post-operative care and therapy.

BACKGROUND

There are many types of post-operative orthotic devices from which doctors and patients may choose. Likewise, there are many types of pain management devices available to aid recovery after surgery. All devices have particular features and drawbacks. Improved devices are always needed, to enable or limit movement in certain directions, to control temperature at a surgical site, to apply or remove pressure on a body part, to rotate, abduct, or adduct a limb, to support or add weight, to stabilize joints, and for various others reasons.

SUMMARY

In an embodiment, a knee brace kit includes a wrap having opposed inner and outer surfaces, and a body and straps extending from the body. The outer surface carries a first engagement element of a hook-and-loop engagement, the straps terminate at tips, and the inner surface at the tips carries a second engagement element of the hook-and-loop engagement complemental to the first engagement element. A hole in the wrap is located such that, when the wrap is worn by a person, the hole is disposed over a knee of the person and the straps are wrapped above and below the hole, defining an applied arrangement of the wrap. There are a plurality of trim lines indicated on the body, which, when the wrap is trimmed along the trim lines, maintain the applied arrangement of the straps with respect to the hole. In the applied arrangement, the tips of the straps are registered, respectively, with the hole, above and below the hole.

In an embodiment, the body includes a proximal end opposite the straps, a top and an opposed bottom. The plurality of trim lines includes proximal vertical trim lines, registered with and inboard of the proximal end of the body, proximal concave trim lines, extending in a concave fashion inboard of the proximal end of the body, and top and bottom concave trim lines, extending in a concave fashion inboard of the top and bottom of the body, respectively. The plurality of trim lines also includes an annular trim line, encircling the hole, a body concavity trim lines, extending in a concave fashion into the body between the straps, horizontal strap trim lines, inboard of and extending along the straps, and strap length trim lines, extending transversely through the straps.

In an embodiment, the kit further includes replacement points for the tips, wherein the replacement points have a lower face carrying the second engagement element applicable to the outer surface of the wrap when the wrap is trimmed along the strap length trim lines such that a portion of the replacement points project outboard of the strap length trim lines which are trimmed. A pocket is applied to the inner surface of the wrap, and a thermal pack carried in the pocket. An annular sheet is secured to the inner surface of the wrap, encircling the hole; the annular sheet carries the first engagement element. Mating elements carrying the second engagement elements are on opposed sides of the mating elements, and the mating elements are engaged to the annular sheet. The pocket has engagement strips which carry the first engagement element. The engagement strips of the pocket are removably engaged to the mating elements.

The above provides the reader with a very brief summary of some embodiments described below. Simplifications and omissions are made, and the summary is not intended to limit or define in any way the disclosure. Rather, this brief summary merely introduces the reader to some aspects of some embodiments in preparation for the detailed description that follows.

BRIEF DESCRIPTION OF THE DRAWINGS

Referring to the drawings.

DETAILED DESCRIPTION

Reference now is made to the drawings, in which the same reference characters are used throughout the different figures to designate the same elements. Briefly, the embodiments presented herein are preferred exemplary embodiments and are not intended to limit the scope, applicability, or configuration of all possible embodiments, but rather to provide an enabling description for all possible embodiments within the scope and spirit of the specification. Description of these preferred embodiments is generally made with the use of verbs such as "is" and "are" rather than "may," "could," "includes," "comprises," and the like, because the description is made with reference to the drawings presented. One having ordinary skill in the art will understand that changes may be made in the structure, arrangement, number, and function of elements and features without departing from the scope and spirit of the specification. Further, the description may omit certain information which is readily known to one having ordinary skill in the art to prevent crowding the description with detail which is not necessary for enablement. Indeed, the diction used herein is meant to be readable and informational rather than to delineate and limit the specification; therefore, the scope and spirit of the specification should not be limited by the following description and its language choices.

Figure 1:
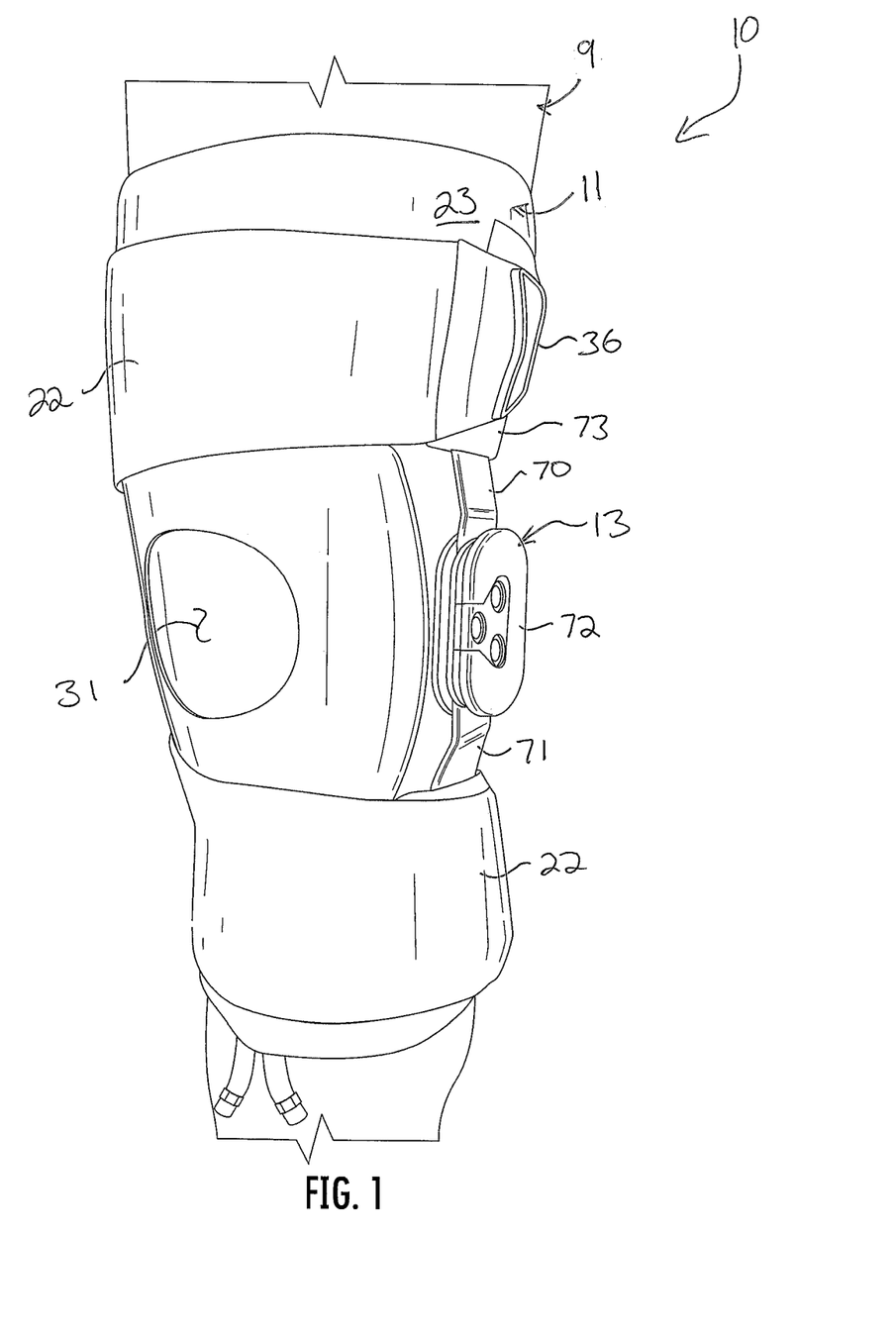
FIG. 1 is a perspective view of modifiable hot/cold therapy knee brace kit.
Figure 2:
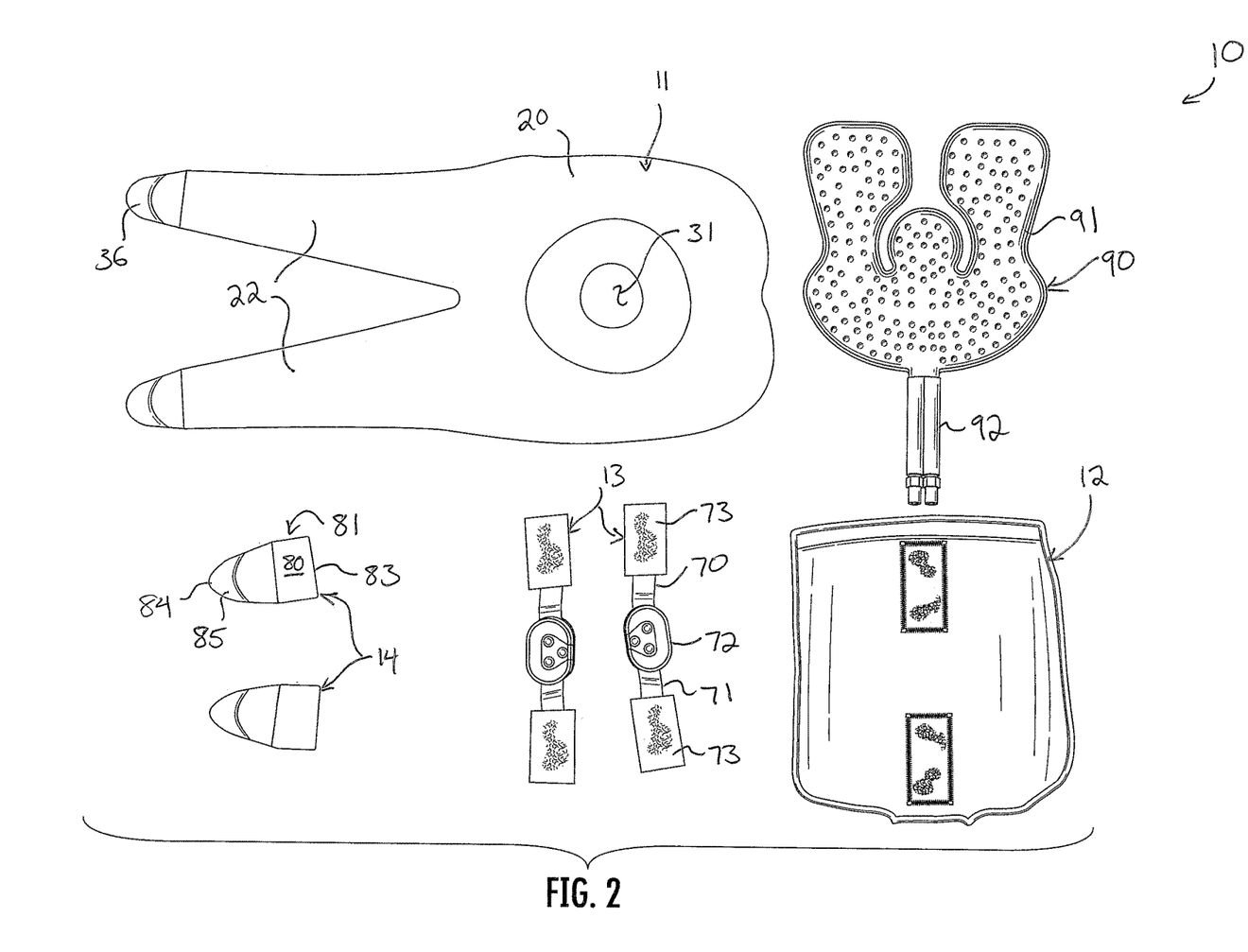
FIG. 2 is a top plan view of elements of the kit of FIG. 1.

FIG. 1 illustrates a modifiable hot/cold therapy knee brace kit (hereinafter, the "kit 10"), applied to and wrapped around the leg 9 of patient. FIG. 2 illustrates the kit 10 in a flat arrangement, with other parts for use in and with the kit 10.

The kit 10 includes a modifiable soft wrap 11, a pocket 12 securable to the wrap 11, two hinges 13, and a two engagement points 14. These parts can be used together in different combinations and can be cut and modified in different combinations and arrangements to be used in different manners and to provide different functionalities.

Figure 3A:
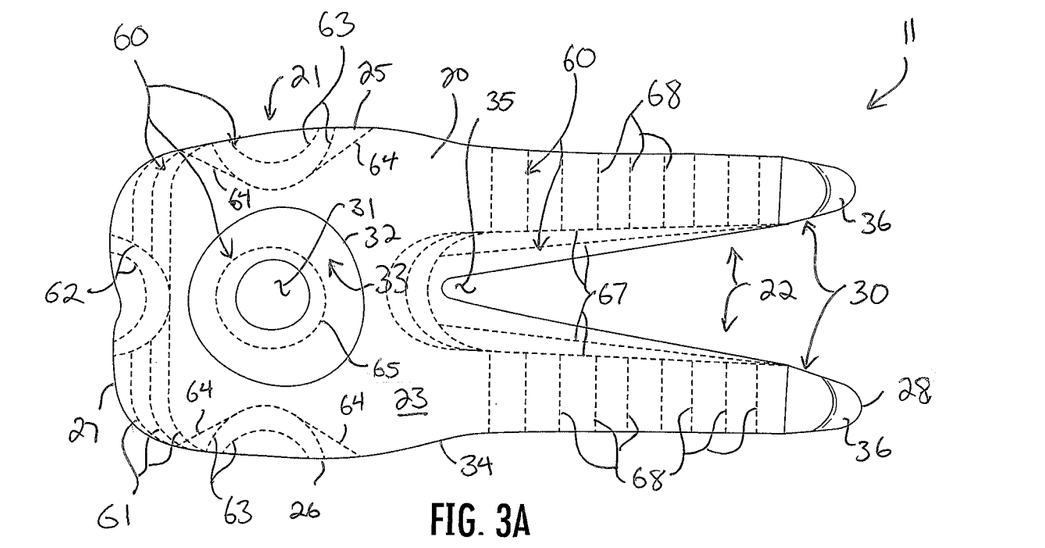
FIGS. 3A and 3B are front and back views of a wrap of the kit of FIG. 1.
Figure 3B:
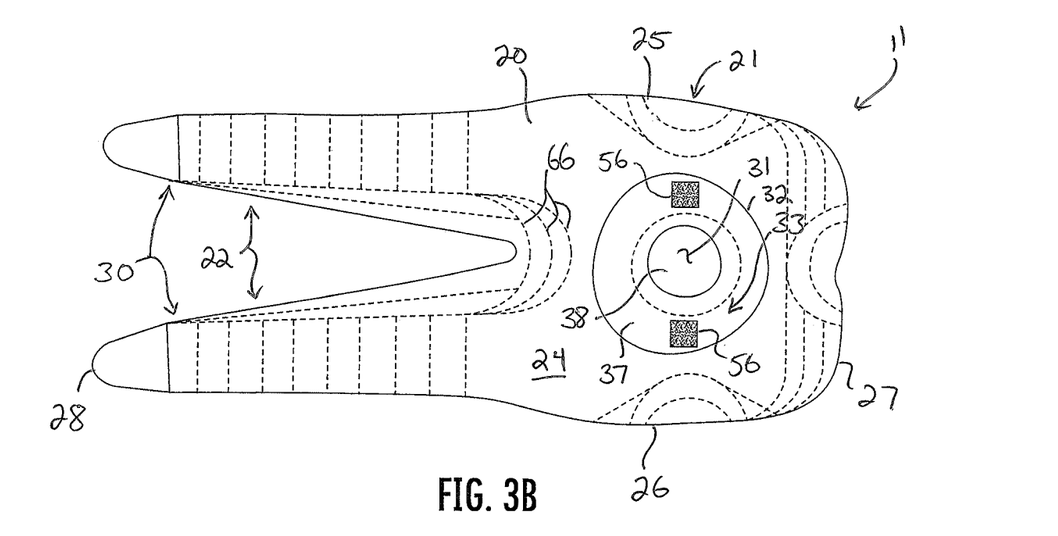

The wrap 11 is shown in detail in FIGS. 3A and 3B. It includes a tooth-shaped sheet 20 having a main body 21 and two straps 22 extending laterally away from the body 21. The body 21 and the straps 22 are formed from the sheet 20, which is preferably a single sheet of flexible, elastic material such as neoprene. The sheet 20 has an outer surface 23 and an opposed inner surface 24. The inner surface 24 is preferably smooth, but the outer surface 23 is preferably covered by an element of a hook-and-loop engagement assembly. When the kit 10 is worn, the inner surface 24 is directed inward toward the leg 9, while the outer surface 23 is directed outward.

The body 21 and straps 22 cooperate to form the continuous, uninterrupted sheet 20 of the wrap 11. The wrap 11 has a top 25, an opposed bottom 26, a proximal end 27, and an opposed distal end 28 of the wrap 11 where the straps 22 terminate in free ends 30. The body 21 has a center, and in this embodiment, a geometric center, in which there is a circular hole 31. The hole 31 is reinforced with stitching around its perimeter. Outside and encircling the hole 31 is a larger-diameter circular stitch 32. An annulus 33 is bound between the hole 31 and the circular stitch 32. The annulus 33 defines a reinforced area of the wrap 11, as is described in more detail below.

Extending from the body 21 laterally are the two straps 22. The straps 22 are identical to each other except with respect to location, and as such, they will be distinguished only by reference to an "upper strap" 22, which is proximate the top 25, or a "lower strap" 22, which is proximate the bottom 26. Otherwise, description herein will be made without particular reference to either strap 22, with the understanding that the description applies equally to both. The strap 22 extends from a base 34 at the body 21 of the wrap 11 to the distal end 28. The strap 22 is wide at the base 34 and narrows consistently from the base 34 to the distal end 28. The base 34 of the strap 22 has a height (aligned parallel to a line extending from the top 25 to the bottom 26) which is approximately just less than half the height between the top 25 and the bottom 26. In this way, the straps 22 are separated by a small gap 35 at their bases 34. This gap 35 enlarges toward the distal end 28 of the wrap 11.

The straps 22 have long inner edges and outer edges. The inner edge of each strap 22 extends from the base 34 to the distal end 28 and is directed toward the other strap 22. The outer edge of each strap 22 similarly extends from the base 34 to the distal end 28, but is directed outward, away from both of the straps 22. The outer edges, when the wrap 11 is laid in the flat arrangement shown in FIGS. 3A and 3B, are generally parallel. The inner edges, however, diverge away from each other as the inner edges extend away from the base 34 to the distal ends 28, such that the gap 35 enlarges in that toward the distal ends 28.

The hook-and-loop engagement element of the wrap 11 covers the outer surface 23 entirely from the proximal end 27 to the free ends 30. However, and preferably but not necessarily, the free ends 30 are different. Each free end 30 is a piece of relatively stiff, strong, inflexible and inelastic material, such as webbing. The outer surface of the free end 30 is smooth. A rubber tip 36 covers the very end of the outer surface proximate the distal end 28. The rubber tip 36 is roughly chevron-shaped and provides a sturdy, non-slip, rugged location from which to grip and pull the free end 30. The rubber tip 36 projects above the outer surface of the free end 30 and above the outer surface 23 of the wrap 11. The inner surface of the rubber tip 36, opposite the outer surface thereof, is covered by an element of the hook-and-loop engagement assembly which is complemental to that on the outer surface 23 of the sheet 20.

FIG. 3B illustrates the back of the wrap 11, showing the inner surface 24 which is presented and applied the leg 9 of the patient. Again, the inner surface 24 has a smooth finish extending entirely from the proximal end 27 to the free ends 30. At the free ends 30, however, the inner surface 24 is covered with the complemental hook-and-loop engagement element. The annulus 33 is reinforced on the back of the wrap 11. An additional annular sheet 37 is sewn onto the inner surface 24 over the annulus 33, between the hole 31 and the circular stitch 32. The annular sheet 37 is coextensive to the annulus 33 and encircles the hole 31. The inner surface of the annular sheet 37, which is directed in the same direction as the inner surface 24 of the wrap 11, is covered with the same engagement element that covers the outer surface 23 of the wrap 11. Thus, the annulus 33 is twice as thick as the rest of the wrap 11.

An elastic panel 38 covers the hole 31. The elastic panel 38 covers the hole 31, provides additional structural support across the hole 31, and acts as a barrier preventing an object from protruding through the hole 31. The panel 38 is coupled, preferably by sewing, to the outer surface 23 of the sheet 20, such that the annular sheet 37 leaves a central hole open on the back side of the kit 10. That central hole is registered with and coextensive to the hole 31. A patient can place his or her hand through that central hole and place it between the inner surface 24 of the annulus 33 and a forward surface of the annular sheet 37.

Figure 4A:
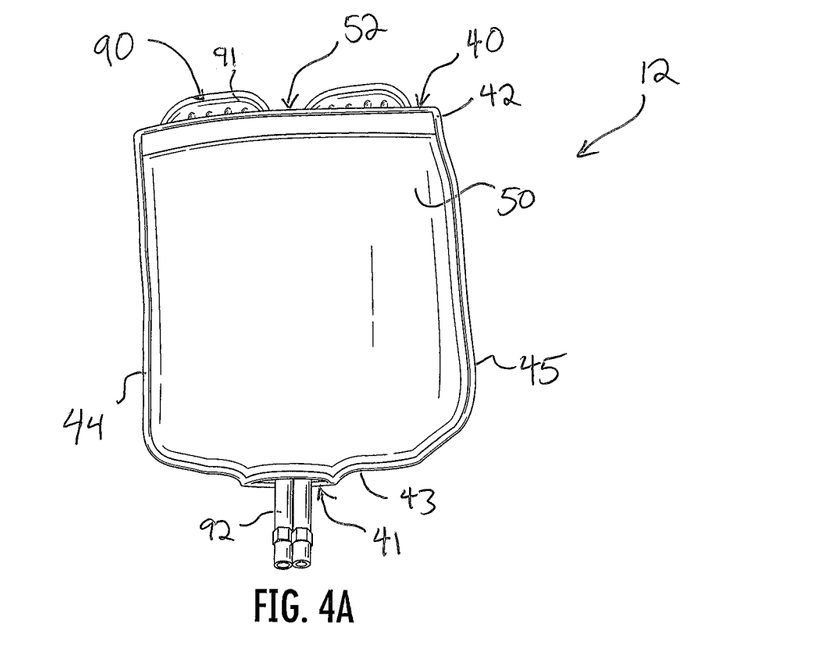
FIGS. 4A and 4B are perspective views of a pocket applied with a thermal pack, both useful with the kit of FIG. 1.
Figure 4B:
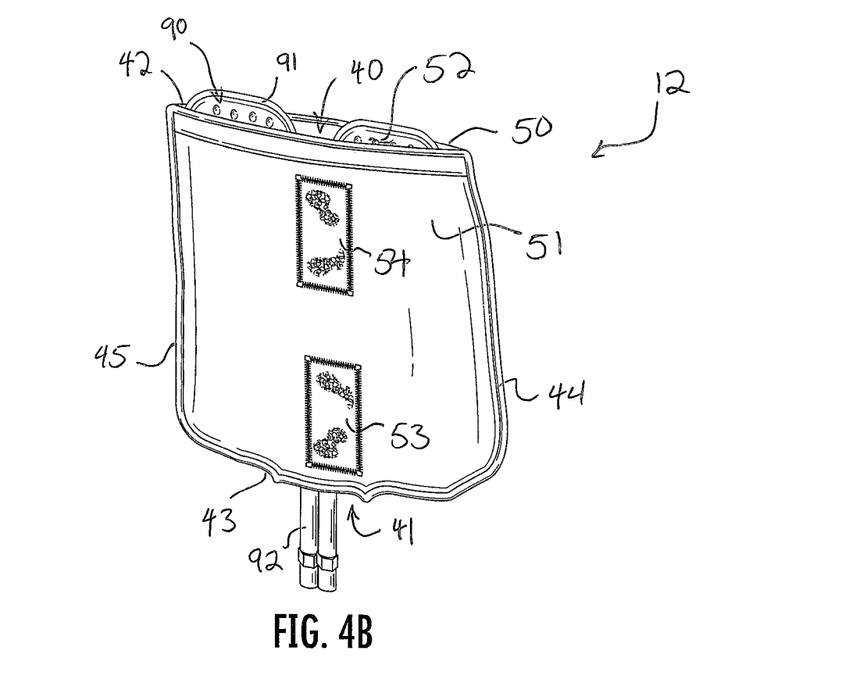

FIGS. 4A and 4B illustrate the pocket 12. The pocket 12 is a flexible pocket, generally rectangular between a wide upper opening 40 at a top 42 of the pocket 12 and a narrow lower opening 41 proximate to a bottom 43 of the pocket 12, and is capable of bending, rolling, and otherwise flexing between and across the top 42 and bottom 43. The pocket 12 has opposed first and second sides 44 and 45 extending entirely between the top 42 and bottom 43. The pocket 12 receives and holds a thermal pack 90, as shown in FIGS. 4A and 4B and FIG. 2.

The pocket 12 is constructed from two flexible panels: a first or inner panel 50 and a second or outer panel 51. The inner panel 50 is prominently shown in FIG. 4A while the outer panel 51 is better shown in FIG. 4B. The inner and outer panels 50 and 51 are fastened to each other, preferably by stitching extending along the first and second sides 44 and 45. The inner and outer panels 50 and 51 are unfastened with respect to each other along the top 42 and the bottom 43, thereby defining the upper and lower openings 40 and 41, respectively. The upper opening 40 is opened entirely between the first and second sides 44 and 45 at the top 42, and the lower opening 41 is opened entirely between the first and second sides 44 and 45 at the bottom 43. Nevertheless, the upper opening 40 is much larger than the lower opening 41. Though it is open, the upper opening 40 can nevertheless be closed by complemental hook-and-loop engagement members on its inner surfaces, or by a clasp or button closure, slideable fastener, or other similar fastening mechanism.

The pocket 12 is shaped like a rounded rectangle. As such, the pocket 12 is wide at the top 42. The first and second sides 44 and 45 extend downward nearly perpendicular from the top 42, and nearly parallel to each other. The first and second sides 44 and 45, just above the bottom 43, curve inward and then terminate just above the lower opening 41. The lower opening 41 has a width between the first and second sides 44 and 45 which is approximately one-fifth the width of the upper opening 40. The lower opening 41 is at the bottom 43 of the pocket 12. The lower opening 41 is a slot formed between the inner and outer panels 50 and 51.

Both the upper and lower openings 40 and 41 lead to an interior 52, defined between the inner and outer panels 50 and 51. The interior 52 has a shape or profile corresponding to that of the pocket 12, and the interior 52 is slim between the inner and outer panels 50 and 51. The interior 52 is thus configured to snugly receive the thermal pack 90. The thermal pack 90 may be a hot pack or a cold pack, such as the one described in U.S. Pat. No. 10,363,159, having a sealed bladder 91 and inlet and outlet tubes 92. The thermal pack 90 is received between the inner and outer panels 50 and 51, and the tubes 92 pass through the lower opening 41 so that they may be connected to supply tubing.

There are attachment points on the pocket 12 that allow the pocket 12 to be attached to the wrap 11. At the bottom 43 of the pocket 12, a hook-and-loop engagement strip 53 is positioned on the outer panel 51. When the kit 10 is worn, the strip 53 faces outward away from the leg 9 of the patient. The engagement strip 53 is positioned on the lower third of the outer panel 51, centrally between the opposed sides 44 and 45, so that its full extent is exposed and available for placement of a complemental hook-and-loop engagement element. At the top 42 of the pocket 12, another hook-and-loop engagement strip 54 is positioned on the outer panel 51, facing outward away from the patient. The engagement strip 54 is positioned on the upper third of the outer panel 51, centrally between the opposed sides 44 and 45, so that its full extent is exposed and available for placement of a complemental hook-and-loop engagement element. The engagement strips 53 and 54 are separated by a gap 55 which is approximately one-third of the height of the pocket 12 between the top 42 and the bottom 43. In the embodiment shown in FIG. 4B, the strips 53 and 54 are sewn onto the outer panel 51, but in other embodiments, the strips 53 and 54 are adhered or attached with complemental hook-and-look engagements to the outer panel 51.

Figure 5A:
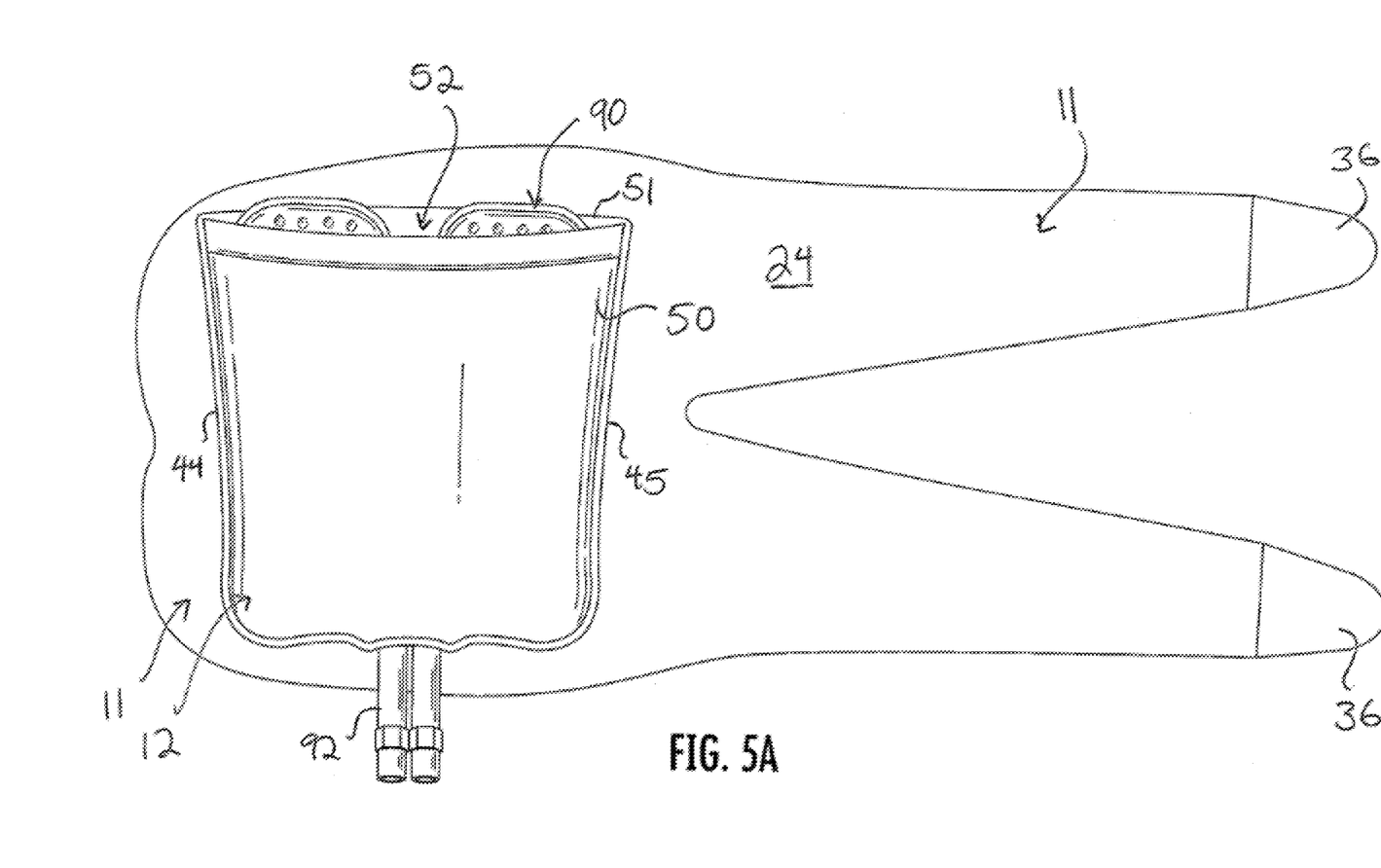
FIG. 5A illustrates the pocket applied to the wrap.

The engagement strips 53 and 54 attach the pocket 12 to the annular sheet 37. The engagement strips 53 and 54 are of the same type of engagement element as that formed on the inner surface of the annular sheet 37; they are not complemental. For example, the engagement strips 53 and 54 and the inner surface of the annular sheet 37 all carry a loop engagement. However, as can be seen in FIG. 3B, two mating elements 56 are attached to the annular sheet 37. These mating elements 56 are squares, removable from and replaceable to the annular sheet 37. The mating elements 56 carry engagement elements on both sides, and they are complemental to the engagements 53 and 54 and to the engagement element on the annular sheet 37. As such, the mating elements 56 engage to both the annular sheet 37 and to the pocket 12 and thereby are useful to secure the pocket 12 to the annular sheet 37. Further, because the mating elements 56 are modular, they can be placed, removed, and replaced as desired to achieve a customized, modified fit. Similarly, because the engagement strips 53 and 54 are elongate, the mating elements 56 can be placed in different positions along the engagement strips 53 to further customize and modify the fit. FIG. 5A shows the pocket 12 engaged to the wrap 11.

Turning back to FIGS. 3A and 3B, the wrap 11 is shown with a larger number and variety of trim lines 60 on the body 21. The trim lines 60 are preferred locations for trimming the kit 10. The kit 10 may be trimmed by a health worker, or by the patient using the kit 10, to modify the kit 10 to both fit the patient and work for the post-operate care. The trim lines 60 are indicated on the body 21; in the embodiment shown in FIGS. 3A and 3B, the trim lines 60 are marked directly on the body 21, on both the inner and outer surfaces 23 and 24. In other embodiments, the trim lines 60 are marked on only one of the inner and outer surfaces 23 and 24. In other embodiments, the trim lines 60 are indicated on the body 21 with markings on instructions accompanying the kit 10. In other embodiments, the trim lines 60 are marked on a removable, transparent sheet overlying one or both of the outer surfaces 23 and 24, which sheet can be cut together with the wrap 11 and removed. In other embodiments, the trim lines 60 are marked on a template, either a full-size or proportional template, and the wrap 11 may be trimmed accordingly. In other embodiments, the trim lines 60 are indicated on the wrap 11 with impressions or perforations made in the body 21 of the wrap 11. Each of these embodiments, and others, represents a manner in which the trim lines 60 are indicated on the body 21.

A first set of trim lines 60 are proximal vertical trim lines 61. Three proximal vertical trim lines 61 are shown, each extending generally between the top 25 and bottom 26 near the proximal end 27 of the body 21. The proximal vertical trim lines 61 are registered with and inboard of the proximal end 27 of the body 21; the edge at the proximal end 27 of the body 21 has a double-humped contour with two convex sections spaced apart by a central concave section therebetween. The proximal vertical trim lines 61 have a similar contour, in which the lines 61 are convex, curving toward the top 25 and bottom 26. The proximal vertical trim lines 61 start and stop on the top 25 and bottom 26. Cutting along any of these lines 61 trims the body 21 down from the proximal end 27, thereby removing portions of the sheet 20 which might otherwise lay on the medial or anterior portion of the leg 9.

A second set of trim lines 60 are proximal concave trim lines 62. Two proximal concave trim lines 62 are shown, each proximate extending arcuately in a concave fashion inboard of, or in from, the proximal end 27. The proximal concave trim lines 62 are centrally located, between the top 25 and bottom 26, and are each concave, extending in from the proximal end 27 toward the hole 31. The proximal concave trim lines 62 start and stop at the proximal end 27, and each intersects the proximal vertical trim lines 61. Cutting along either of these lines 62 carves out a concavity in the body 21 by the proximal end 27.

A third set of trim lines 60 are top and bottom concave trim lines 63. There are preferably but not necessarily two lines 63 proximate each of the top 25 and bottom 26. The lines 63 proximate the top 25 start and stop at the top 25, and the lines 63 proximate the bottom 26 start and stop at the bottom 26. The lines 63 are centrally located on the body 21, generally registered with the hole 31, and each extends in a concave fashion inboard of the top and bottom of the body toward the hole 31.

A fourth set of trim lines 60 are top and bottom linear trim lines 64, of which there are preferably but not necessarily two lines 64 proximate each of the top 25 and bottom 26. Theses lines 64 are linear, starting at the top 25 and bottom 26 and then extending directly toward the concave trim lines 63. Cutting along any of these lines 63 and 64 carves out either an arcuate or an angular concavity in the top 42 or bottom 43.

A fifth trim line 60 is an annular trim line 65. The annular trim line 65 is a single line encircling the hole 31. The annular trim line 65 is roughly circular and is radially spaced apart from the hole 31. Cutting along this line 65 enlarges the hole 31 and removes the elastic panel 38, but retains the annulus 33 without removing it.

A sixth set of trim lines 60 are body concavity trim lines 66. Three of these lines 66 are shown, extending arcuately and concavely inward on the body 21 from between the bases 34 of the straps 22. The body concavity trim lines 66 start at the trim lines 67 (below) on the upper strap 22, curve in a concave fashion into the body 21, then terminate at the opposed trim line 67 on the lower strap 22. Cutting along these lines 66 enlarges the gap 35 between the straps 22 and inward into the body 21.

A seventh set of trim lines 60 are horizontal strap trim lines 67. There are two of these lines 67 along the bottom of the upper strap 22 and two of these lines 67 along the top of the lower strap 22. These lines 67 are inboard of the inner edges of the straps 22 and extend horizontally from the base 34 of the straps 22 laterally outward until they terminate just short of the distal ends 28. The lines 67 start at the body concavity trim lines 66 and then terminate on the edges of the straps 22 inboard of the distal ends 28. Cutting along these lines 67 narrows the straps 22 and enlarges the gap 35 between the straps 22.

An eight set of trim lines 60 are strap length trim lines 68. Nine such trim lines 68 are shown in this embodiment, though there may be a greater or lesser number of trim lines 68 in other embodiments. These lines 68 extend vertically, or transversely, through the straps 22. The strap length trim lines 68 start at the outer edges of the straps 22. The lines 68 proximate the distal ends 28 terminate on the opposed inner edge of the straps 22, and the lines 68 further away from the distal ends 28 terminate on the horizontal strap trim lines 67. Cutting along these lines 68 cuts the free ends 30 of the straps 22 off and shortens the lengths of the straps 22.

Figure 6:
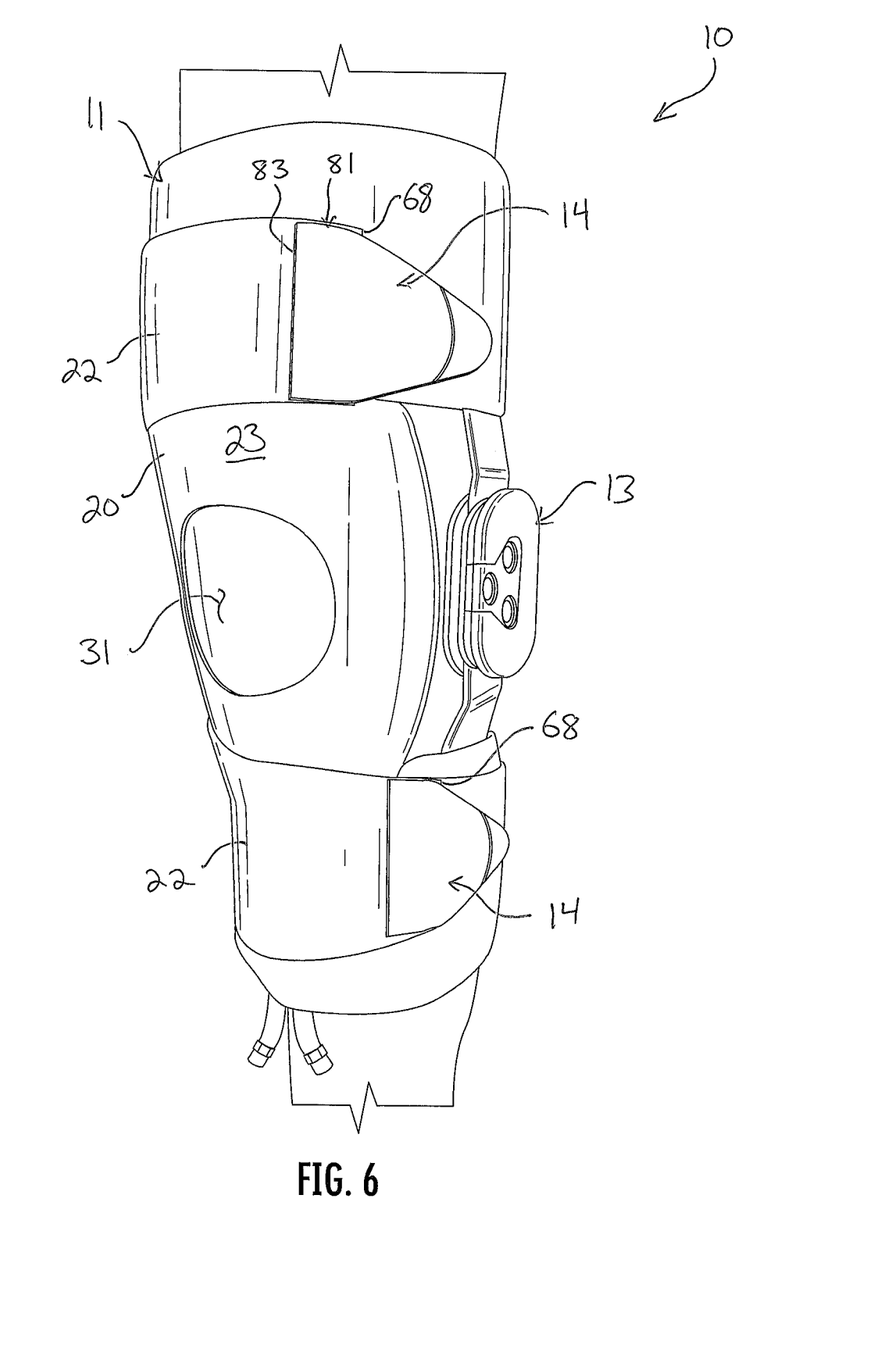
FIG. 6 is a perspective view of the kit of FIG. 1 with tips applied to trimmed ends of the wrap.

The above trim lines 60 are not exclusive; other embodiments of the kit 10 have other trim lines, and other embodiments have other numbers of the trim lines 61-68 than shown and described here. Further, FIG. 6 shows the trim lines 60 marked on the wrap 11 itself. In some embodiments, the wrap 11 is marked with each of the lines 60 on either or both of the outer and inner surfaces 23 and 24 to allow the health worker or patient to easily cut the wrap 11 along the trim lines 60. In other embodiments, the wrap 11 is not marked.

Figure 5B:
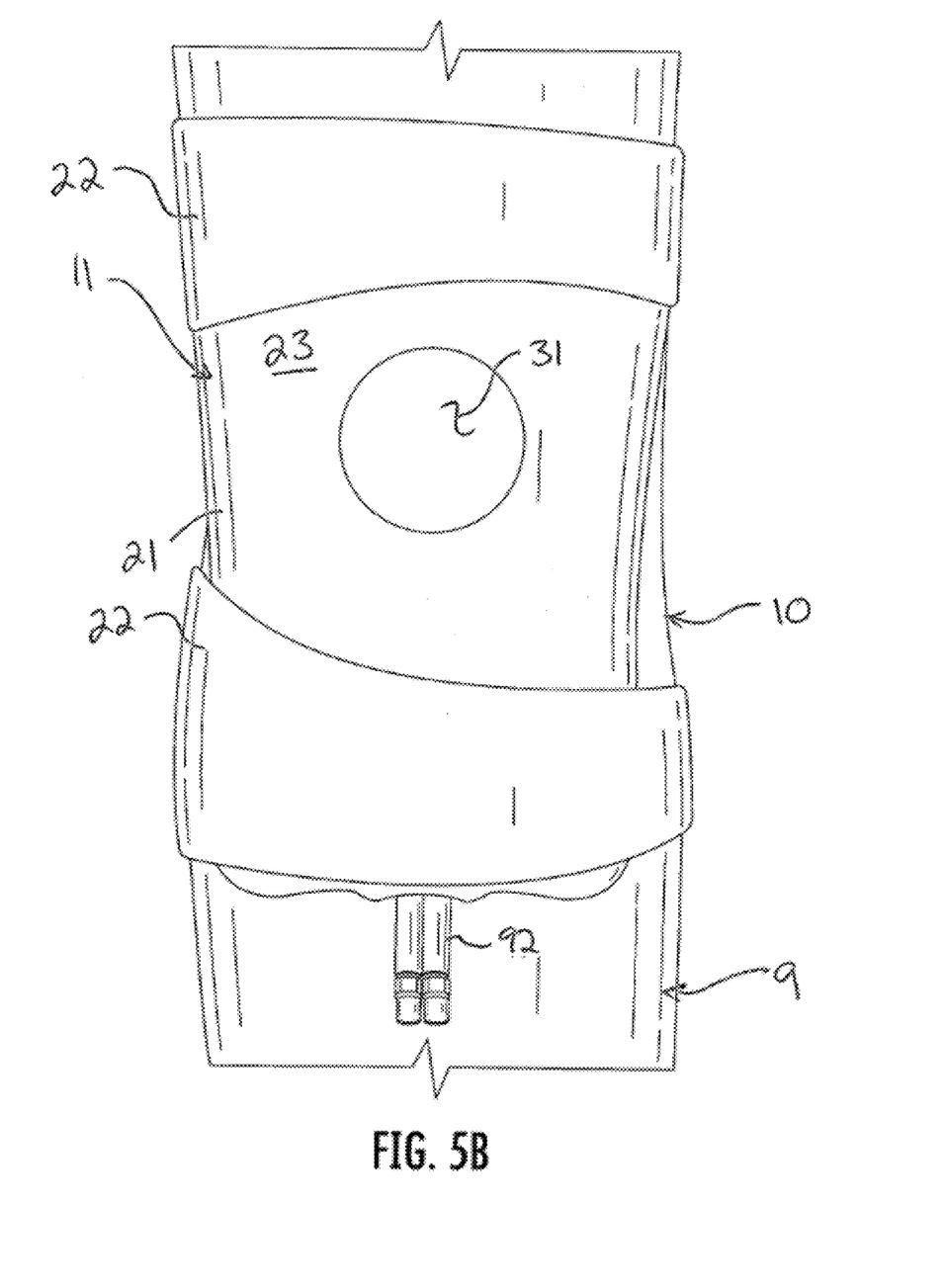
FIG. 5B illustrates the pocket applied to the wrap, wrapped around a leg of a patient.
Figure 5C:
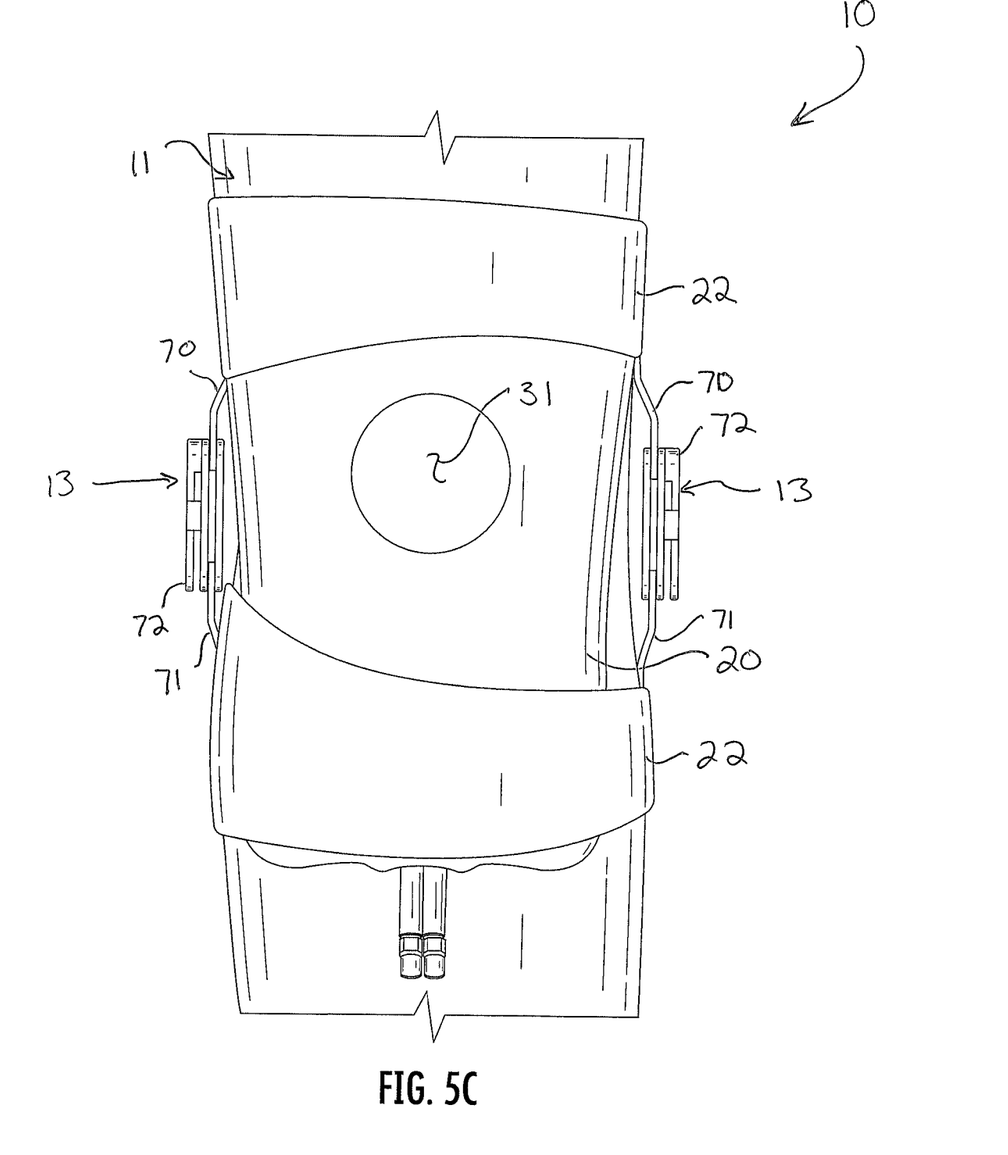
FIG. 5C illustrates the pocket applied to the wrap, wrapped around a leg of a patient, and used with hinges.

In operation, the wrap 11 is useful for stabilizing a knee after surgery or a medical procedure. Referring now primarily to FIGS. 5A and 5B, the thermal pack 90 is applied to the interior 52 of the pocket 12 and the pocket 12 is secured to the wrap 11. The engagement strips 53 and 54 (not visible) attached to the outer panel 51 engage with the mating elements 56 (also not visible) on the annulus 33 on the inner surface 24 of the wrap 11. The inlet and outlet tubes 92 are oriented so as to clear the body 21 of the wrap 11.

With the thermal pack 90 applied to the wrap 11, the wrap 11 can now be wrapped around the leg 9, as in FIG. 5B. The hole 31 is placed over the kneecap, with the inner surface 24 against the patient's skin. The straps 22 are wrapped around the patient's leg 9 and then secured on the outer surface 23 of the wrap 11 (preferably on the outer surface 23 of the body 21). FIG. 5B defines an applied arrangement of the kit 10, in which the wrap 11 is worn on the leg 9 of a person, the hole 31 is disposed over the knee of the person, and the straps 22 are wrapped above and below the hole 31, registered therewith. The kit 10 shown in FIG. 5B is suitable for administration of cold or heat therapy. The thermal pack 90 supplies either hot or cold fluid through the tubes 92. When the wrap 11 is worn in this applied arrangement, the thermal pack 90 is disposed over and around the knee, as shown in FIG. 5B, to enhance recovery.

If desired, the wrap 11 can be modified with a hinge kit. FIGS. 1, 2, 5C, and 6 each show the hinges 13. Referring primarily to FIGS. 1 and 2, the kit 10 preferably uses two, mirror-identical hinges 13. Because the hinges 13 are mirror identical, only one is described herein with the understanding that the description applies equally to both. Each hinge 13 has an upper arm 70, a lower arm 71, and a hinge or pivot 72 coupling the upper and lower arms 70 and 71 for hinged movement. Moreover, both the upper and lower arms 70 and 71 carry pads 73 which are covered with engagement elements. The hinges 13 are placed on the outer surface 23 of the wrap 11 flanking the hole 31. The hinges 13 support the knee and prevent unwanted lateral movement of the knee. The pads 73 attached to the engagement element covering the outer surface 23 of the wrap 11 and are positionable in a large variety of locations around the knee.

The above modifications are non-permanent. If desired, the wrap 11 can be cut to permanently modify it. Cutting along any of the trim lines 61 changes the structure, configuration, and function of the kit 10. However, when the trap is trimmed along any of the trim lines 60, the cuts allow the patient to maintain the applied arrangement of the wrap 11; the patient can still wrap the straps 22 around the leg 9 of the patient and apply them back on the outer surface 23 of the wrap 11, placing the cut ends in registered locations above and below the hole 31. Cutting along the strap length trim lines 68 will remove the free ends 30, which would otherwise prevent the straps 22 from being wrapped around and secured back on the outer surface 23 of the wrap 11. However, the kit 10 includes the replacement points 14, which are replacements for the removed free ends 30 and the tips 36 thereon.

The points 14 are shown in FIG. 1. The points 14 are identical in every respect and description is made with respect to only one, with the understanding that the description herein applies equally to both. The point 14 has an upper face 80, which is visible in FIG. 1, and an opposed lower face 81, which is not visible in FIG. 1 but is opposed to the upper face 80. The point 14 is a piece of relatively stiff, strong, inflexible and inelastic material, such as webbing. The point 14 has a large, flat butt end 83 and an opposed curved end 84. The upper face 80 is smooth. A rubber tip 85 covers the curved end 84 of the point 14. The rubber tip 85 is roughly chevron-shaped and provides a sturdy, non-slip, rugged location from which to grip and pull the point 14. The rubber tip 85 projects above the upper face 80, so that it may be more easily grabbed.

The lower face 81 is covered by an element of the hook-and-loop engagement assembly which is complemental to that on the outer surface 23 of the sheet 20. In this way, once the straps 22 are cut along the strap length trim lines 68, the lower face 81 at the butt end 83 of the point 14 is engaged against the outer surface 23 of the strap 22 proximate its cut. The lower face 81 at the curved end 84 of the point 14 is left uncovered by the strap 22, such that the point 14 extends beyond the trimmed trim line 68. This uncovered portion of the lower 81 can then be engaged to the outer surface 23 of the wrap 11.

The replacement points 14 are useful when any length of the straps 22 are trimmed for a slender leg. As shown in FIG. 6, the kit 10 has been trimmed along a strap length trim line 68. Once the straps 22 are trimmed, however, there is no way to secure them to the outer surface 23 of the wrap 11 but for the points 14. The replacement points 14 are thus applied to the cut straps 22. The hook-and-loop engagement element on the lower face 81 proximate the butt end 83 is engaged with the complemental hook-and-loop engagement element on the outer surface 23 of the strap 22 proximate the trim line 68, such that the curved end 84 of the point 14 projects off of or outboard of the strap 22 beyond the trim line 68 where its lower face 81 is available to be—and actually is— engaged with the underlying outer surface 23. In this way, the strap 22 is wrapped around the leg and attached back on outer surface 23 of the wrap 11, thereby securing the wrap 11 on the leg 9 of the patient. The kit 10 and parts thereof may thus be cut, modified, used, ignored, and/or combined in different variations to change the structure and function of the kit 10, and the kit 10 can be continued to use in the applied arrangement with the replacement points 14 registered above and below the hole 31.

A preferred embodiment is fully and clearly described above so as to enable one having skill in the art to understand, make, and use the same. Those skilled in the art will recognize that modifications may be made to the description above without departing from the spirit of the specification, and that some embodiments include only those elements and features described, or a subset thereof. To the extent that modifications do not depart from the spirit of the specification, they are intended to be included within the scope thereof.

What is claimed is:

1. A knee brace kit comprising:
    a wrap having:
        opposed inner and outer surfaces, the outer surface carrying an engagement element of a hook-and-loop engagement having a first of a hook type engagement or a loop type engagement;
        a body; and
        straps extending from the body and terminating at tips, an inner surface at the tips carrying an engagement element having a second of the hook type engagement or the loop type engagement that is complemental to the first of the hook type engagement or the loop type engagement;
    a hole in the wrap located such that, when the wrap is worn by a person, the hole is disposed over a knee of the person and the straps are wrapped above and below the hole, defining an applied arrangement;
    an annular sheet secured to the inner surface of the wrap, encircling the hole, wherein the annular sheet carries an engagement element having the first of the hook type engagement or the loop engagement;
    mating elements having the second of the hook type engagement or the loop type engagement on opposed sides of the mating elements, the mating elements being removably engaged to the annular sheet;
    a pocket applied to the inner surface of the wrap, the pocket having engagement strips having the first of the hook type engagement or the loop type engagement such that the engagement strips of the pocket are removably engaged to the mating elements; and
    a thermal pack carried in the pocket.

2. The knee brace kit of claim 1, wherein in the applied arrangement, the tips of the straps are registered, respectively, with the hole, above and below the hole.

3. The knee brace kit of claim 1, further comprising a plurality of trim lines indicated on the body, which, when the wrap is trimmed along the trim lines, maintain the applied arrangement of the straps with respect to the hole.

4. The knee brace kit of claim 3, wherein:
    the body includes a proximal end opposite the straps, a top and an opposed bottom; and
    the plurality of trim lines includes:
        proximal vertical trim lines, registered with and inboard of the proximal end of the body;
        proximal concave trim lines, extending in a concave fashion inboard of the proximal end of the body;
        top and bottom concave trim lines, extending in a concave fashion inboard of the top and bottom of the body, respectively;
        an annular trim line, encircling the hole;
        body concavity trim lines, extending in a concave fashion into the body between the straps;
        horizontal strap trim lines, inboard of and extending along the straps; and
        strap length trim lines, extending transversely through the straps.

5. The knee brace kit of claim 4, further comprising replacement points for the tips, wherein the replacement points each have a lower face carrying an engagement having the second of the hook type engagement or the loop type engagement applicable to the outer surface of the wrap when the wrap is trimmed along the strap length trim lines such that a portion of the replacement points project outboard of the strap length trim lines which are trimmed.

6. The knee brace kit of claim 1, further comprising replacement points for the tips, wherein the replacement points each have a lower face carrying an engagement element having the second of the hook type engagement or the loop type engagement applicable to the outer surface of the wrap.

7. A knee brace kit comprising:
    a wrap having:
        opposed inner and outer surfaces, the outer surface carrying an engagement element of a hook-and-loop engagement having a first of a hook type engagement or a loop type engagement;
        a body; and
        straps extending from the body and terminating at tips, an inner surface at the tips carrying an engagement element having a second of the hook type engagement or the loop type engagement that is complemental to the first of the hook type engagement or the loop type engagement;
    a hole in the wrap located such that, when the wrap is worn by a person, the hole is disposed over a knee of the person and the straps are wrapped above and below the hole, defining an applied arrangement;
    strap length trim lines, indicated on and extending transversely through the straps, which, when the wrap is trimmed along the strap length trim lines, maintain the applied arrangement of the straps with respect to the hole; and
    replacement points for the tips, wherein the replacement points each have a lower face carrying an engagement element having the second of the hook type engagement or the loop type engagement applicable to the outer surface of the wrap when the wrap is trimmed along the strap length trim lines such that a portion of the replacement points project outboard of the strap length trim lines which are trimmed.

8. The knee brace kit of claim 7, further comprising:
    a pocket applied to the inner surface of the wrap; and
    a thermal pack carried in the pocket.

9. The knee brace kit of claim 8, further comprising:
an annular sheet secured to the inner surface of the wrap, encircling the hole, wherein the annular sheet carries an engagement element having the first of the hook type engagement or the loop type engagement;
mating elements having the second of the hook type engagement or the loop type engagement on opposed sides of the mating elements, wherein the mating elements are removably engaged to the annular sheet;
wherein the pocket has engagement strips having the first of the hook type engagement or the loop type engagement; and
wherein the engagement strips of the pocket are removably engaged to the mating elements.

10. The knee brace kit of claim 7, wherein in the applied arrangement, the tips of the straps are registered, respectively, with the hole, above and below the hole.

11. The knee brace kit of claim 7, further comprising a plurality of trim lines indicated on the body, which, when the wrap is trimmed along the trim lines, maintain the applied arrangement of the straps with respect to the hole.

12. The knee brace kit of claim 11, wherein:
the body includes a proximal end opposite the straps, a top and an opposed bottom; and
the plurality of trim lines includes:
proximal vertical trim lines, registered with and inboard of the proximal end of the body;
proximal concave trim lines, extending in a concave fashion inboard of the proximal end of the body;
top and bottom concave trim lines, extending in a concave fashion inboard of the top and bottom of the body, respectively;
an annular trim line, encircling the hole;
body concavity trim lines, extending in a concave fashion into the body between the straps; and
horizontal strap trim lines, inboard of and extending along the straps.

\* \* \* \* \*